United States Patent [19]

Bertram

[11] Patent Number: 5,355,874
[45] Date of Patent: Oct. 18, 1994

[54] OROPHARYNGEAL DEVICE

[76] Inventor: Volker Bertram, Robert-Bosch-Str. 7, 7247 Sulz a.N., Fed. Rep. of Germany

[21] Appl. No.: 915,702
[22] PCT Filed: Nov. 21, 1991
[86] PCT No.: PCT/EP1/021970
  § 371 Date: Jul. 22, 1992
  § 102(e) Date: Jul. 22, 1992
[87] PCT Pub. No.: WO92/09325
  PCT Pub. Date: Jun. 11, 1992

[30] Foreign Application Priority Data

Nov. 22, 1990 [DE] Fed. Rep. of Germany ....... 4037084

[51] Int. Cl.⁵ ............................................. A61M 16/00
[52] U.S. Cl. ............................ 128/200.26; 128/207.14
[58] Field of Search ................... 128/200.26, 206.29, 128/207.14, 207.15, DIG. 26

[56] References Cited

U.S. PATENT DOCUMENTS

| | | | |
|---|---|---|---|
| 1,498,810 | 6/1924 | Poe | 128/200.26 |
| 2,705,959 | 4/1955 | Elmore . | |
| 2,820,457 | 1/1958 | Phillips . | |
| 3,419,004 | 12/1968 | Bermann | 128/207.14 |
| 3,774,616 | 11/1973 | White et al. | 128/200.26 |
| 3,908,665 | 9/1975 | Moses | 128/207.14 |
| 3,926,196 | 12/1975 | Bornhorst et al. | 128/207.14 |
| 3,930,507 | 1/1976 | Berman | 128/207.14 |
| 4,067,331 | 10/1978 | Bermann | 128/200.26 |
| 4,270,529 | 6/1981 | Muto | 128/200.26 |
| 4,919,126 | 4/1990 | Baildon | 128/207.14 |

FOREIGN PATENT DOCUMENTS 2848592 5/1980 Fed. Rep. of Germany .

OTHER PUBLICATIONS

"Der Anaesthesist", vol. 13, part 5, May 1964; pp. 172 and 173.

Primary Examiner—Edgar S. Burr
Assistant Examiner—Aaron J. Lewis
Attorney, Agent, or Firm—Michael J. Striker

[57] ABSTRACT

The oropharyngeal device has an extended body including a comparatively shorter approximately straight portion and a comparatively longer curved portion adjoining the straight portion. The extended body has a substantially constant U-shaped transverse cross-section along its entire length thus providing a U-shaped opening on one side thereof; a transverse securing flange attached to an end of the straight portion remote from the curved portion, one side of the transverse securing flange being provided with a U-shaped first recess, the first recess conforming to the U-shaped transverse cross-section of the extended body and positioned to provide a mouth for the U-shaped opening, and also with a C-shaped second recess in a side of the transverse securing flange remote from the side having the U-shaped first recess, the C-shaped second recess being dimensioned so that an endotracheal tube can be snapped in the second recess and held fixed therein; and a hard bite block formed integrally with the tube body and located in the vicinity of the straight portion, the bite block being made of a material also used for making the extended body.

11 Claims, 2 Drawing Sheets

OROPHARYNGEAL DEVICE

BACKGROUND OF THE INVENTION

An oropharyngeal tube is fitted to a patient after intubation by a tracheal tube and serves a number of purposes:

firstly it is intended to keep the airway open artificially and secondly to allow a cannula to be introduced at any time via the tube for the purpose of aspirating secretions, and furthermore, the tube should act as a bite block to prevent the inserted tracheal tube from being squeezed off or even bitten off.

In addition, the oropharyngeal tube should, as far as possible, hold the tongue and prevent it from falling back and closing the airways. This results in the anatomical shape of the tube which comprises, in succession as seen from the side, a transverse securing flange, which is located externally on the patient's lips, an adjoining short, substantially straight portion and in turn, adjoining the latter, a long, curved portion.

There are two fundamentally different types of pharyngeal tube:

The Berman type has an open cross-section, generally a T or double-T profile. Since it is not possible to incorporate a bite block, this oropharyngeal tube is always made of a hard material.

The Guedel type has a closed, generally transverse oval cross-sectional shape. Either it consists entirely of hard material or the actual tube consists of soft rubber or plastics, it being necessary to provide in the region of the straight portion a bite block of hard material which is generally a separate part that is pushed over the actual tube. Such oropharyngeal tubes are described, for example, in the January 1978 edition of the journal "Health Devices" in the article "Artificial Airways" starting on page 67.

Furthermore, it is known to use such a tube also for securing the inserted tracheal tube, in that the holding means for the oropharyngeal tube simultaneously holds the tracheal tube.

Such a solution, in which the holding means for the two tubes comprises a rubber band extending around the patient's neck, is described in an article from "Der Anästhesit" (The Anaesthetist), Vol. 13, part 5, May 1964, pages 172 and 173, Springer-Verlag, Berlin, under the title "Eine einfache Haltevorrichtung für Endotracheal-Katheter" (A simple holding device for endotracheal catheters) by J. Schara, but the oropharyngeal tube used therein is a known Guedel tube supplemented by an advantageous holding means.

The known oropharyngeal tubes have a number of disadvantages:

The closed cross-sectional shape of the Guedel type gives rise to problems with the cleaning of the tube for reuse, since it is very difficult to monitor the state of cleanliness.

Putting together the actual tube and an additional bite block is disadvantageous, since the internal diameter is not uniform and therefore there is a step between the bite block and the tube which 1. gives rise to poor throughflow rates,
2. creates a contamination site with the risk of infection,
3. gives rise to re-use problems because of the poor scope for cleaning, and
4. makes it relatively difficult to insert an aspiration catheter.

As a result of its cross-sectional shape the Berman type has a large number of free edges which, because it always has to be made of hard material, can easily result in injury to the patient.

The described holding means also has shortcomings, since every time the holding means for the oropharyngeal tube is released the tracheal tube is automatically also detached from its securing means, so that in such a case the tracheal tube can very easily become dislodged or slip out. The greatest disadvantage is, however, that access to the mouth for cleaning purposes is almost completely blocked, and aspiration is difficult to carry out, even via the tube. From the point of view of manufacture, this tube with the band is far too expensive.

It is an object of the present invention, therefore, to provide an oropharyngeal tube that is simple and risk-free in use, that is re-usable but is nevertheless simple and inexpensive to produce and, furthermore, enables the tracheal tube to be reliably secured.

According to the invention, the oropharyngeal device comprises an extended body having a comparatively shorter approximately straight portion and a comparatively longer curved portion adjoining the straight portion, the extended body having a substantially constant U-shaped transverse cross-section along an entire length thereof to provide a U-shaped opening extending along one side thereof; a transverse securing flange attached to an end of the straight portion remote from the curved portion; and a hard bite block formed integrally with the extended body and located in the vicinity of the straight portion. The bite block is made of a material also used for the extend body. One side of the transverse securing flange is provided with a U-shaped first recess conforming to the U-shaped transverse cross-section of the extended body and a second recess in a side of the securing flange remote from the side having the U-shaped first recess. The U-shaped first recess is positioned in the securing flange to provide a mouth for the U-shaped opening. The second recess is C-shaped and is dimensioned so that an endotracheal tube can be snapped therein and held fixed therein.

In a preferred embodiment of the invention the extended body has a wall thickness such that the tube body is elastic over the entire length thereof but cannot at least cannot be closed by compression or compressed in operation. Preferably the wall thickness of the straight portion is twice the wall thickness of the curved portion.

The extended body in an additional embodiment can have a longitudinally extending advantageously concave channel on a side opposite to the U-shaped opening, the channel having a base in alignment with a base of the C-shaped second recess.

Advantageously a smallest distance between the longitudinally extending channel and the U-shaped opening of the extended body is greater than a wall thickness of the extended body. Also in a preferred embodiment a height of the cross-section in the straight region of the extended body is greater in the vicinity of the smallest distance than in the vicinity of the U-shaped opening.

At least one perpendicularly projecting extension piece can be provided at the base of the C-shaped second recess extending from a side of the transverse securing flange remote from the extended body. The extension piece can have a length approximately equal to at least a width of a plaster strip and has a thickened portion at a free end thereof. The device can also have two fastening means for insertion into a fastening band, the fastening means being attached to the transverse securing flange and extending from a side of the securing flange remote from the extended body. Each of the fastening means has a projecting nipple protruding above and below a center of the transverse securing flange and the transverse securing flange is provided with two eyelets through which the fastening band can be passed.

Because the device of the invention is closed on one side and is open on the other side, firstly it is possible to insert it easily and with little risk of injury and, secondly, the open side allows the inside surface to be cleaned simply and thoroughly. Because the inside surface is constant and U-shaped, an aspiration catheter can be introduced into the tube very easily, that is to say with little resistance.

In contrast, in the known tubes or devices the inside surface is reduced in the region of the bite block.

The fact that the bite block is made of the same material as the whole device and is formed integrally therewith simplifies and reduces the cost of manufacture which can then be effected using an injection molding process.

The material chosen is a plastics material which has adequate resistance where the material is thicker, such as in the region of the bite block, but which enables the material thickness chosen for the curved portion of the extended body to be such that there the extended body is elastic in its longitudinal direction, that is to say deviating from the curved shape of its rest condition, while the U-shaped cross-section cannot be deformed by any action of the intubated patient, that is to say there is no risk of this artificial airway becoming compressed.

The second recess in the securing flange and the C-shape thereof allows a tracheal tube to be pushed in and locked into place. In addition to this holding means, the tracheal tube can be secured, by strips of plaster, to a corresponding extension piece extending outwards from the securing flange on the side remote from the extended body. The length thereof must correspond to at least the width of the strip of plaster and there is preferably a thickened portion on the free end of the extension piece to prevent the plaster strip from slipping off.

The secure position of the tracheal tube on the oropharyngeal tube is further increased by a channel extending in the longitudinal direction on the narrow side of the central portion, which channel is located on the narrow side opposite the U-shaped inside surface and in which channel a tracheal tube that is pressed into the C-shaped recess of the securing flange comes to rest. The channel has a curved cross-sectional shape the base of which is in alignment with the base of the C-shaped recess in the securing flange.

Bite protection is achieved by providing that the material thickness in the region of the central portion between the U-shaped inside surface and the channel is always greater than the material thickness in the region of the curved portion. In addition, the cross-section in this central portion, seen in elevation, is greater than at the side in the region of the U-shaped inside surface.

Furthermore, the extended body according to the invention can be fastened using securing devices, preferably using nipples that project forwards from the securing flange, by means of a rubber band around the rear of the head or neck of the patient. A tracheal tube that is rigidly connected to the oropharyngeal extended body in the described manner is also securely held thereby.

BRIEF DESCRIPTION OF THE DRAWINGS

An embodiment according to the invention is described in more detail by way of example in the drawings.

DETAILED DESCRIPTION OF THE PREFERRED EMBODIMENTS

Figure 1:
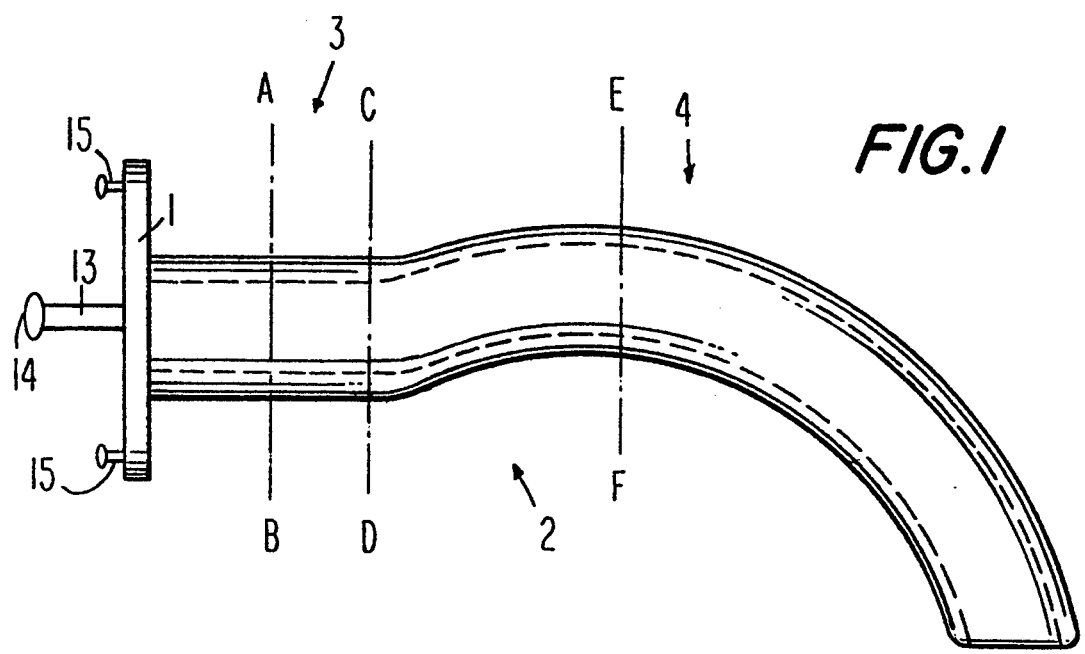
FIG. 1 is a side view of the oropharyngeal tube.

FIG. 1 shows in side view—like all positional details, referring to the in situ position of the device—the typical form of an oropharyngeal device: in the side view it is possible to see the securing flange 1 from which extend, in one direction, i.e. away from the patient, the nipples 15 for securing a rubber or fastening band 27, and the extension piece 13 with its thickened portion 14 at the free end, and the two eyelets 20. In the other direction, adjacent to the securing flange 1, there is first a short, approximately straight portion 3 and in turn, adjacent to the latter, a long, curved portion 4, which portions together form the extended body 2. Where the short portion 3 merges into the long curved portion 4 there is a slight kink, in conformity with the anatomical conditions at the site of use.

Figure 2:
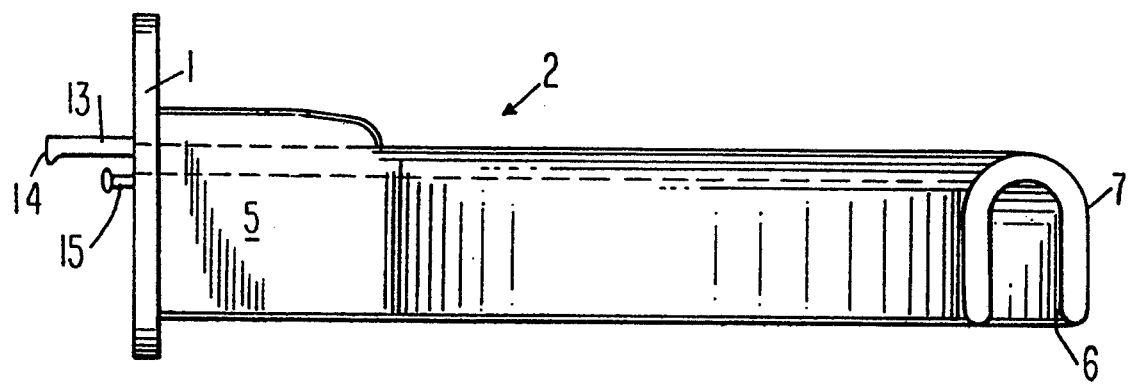
FIG. 2 is a plan view of the tube shown in FIG. 1 from below.

FIG. 2 shows the same oropharyngeal device viewed from below. At its free end, which is slanted relative to the longitudinal axis of the extended body and lies approximately perpendicular to the plane of the securing flange, the U-shaped opening 6 has a constant cross-section over the entire length of the tube body. In the region of the long, curved portion 4, the external contour 7 also is U-shaped, FIG. 2 also showing the wall thickness 12 of the extended body at the free end, which thickness remains the same over the whole of portion 4, but in other embodiments can decrease towards the free end.

As shown by dotted lines in FIGS. 1 and 2, the U-shaped opening 6 is unchanged over the entire length of the extended body 2 and conforms also to the first, U-shaped recess 8 in the securing flange 1 through which proves a mouth for it.

Figure 3:
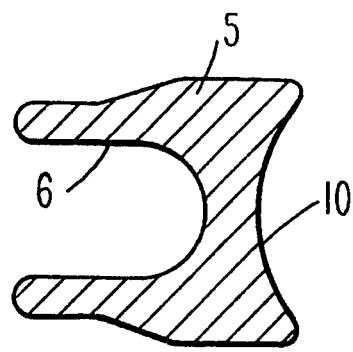
FIG. 3 is a cross-sectional view through the tube taken along the section line A-B of FIG. 1.
Figure 4:
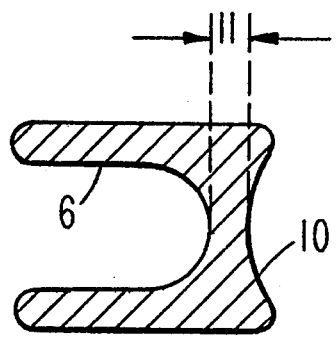
FIG. 4 is a cross-sectional view through the tube taken along the section line C-D of FIG. 1.
Figure 5:
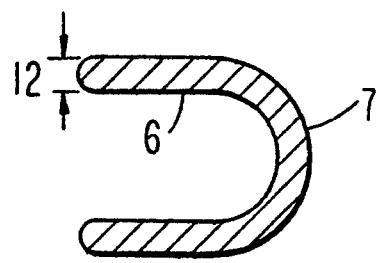
FIG. 5 is a cross-sectional view through the tube taken along the section line E-F of FIG. 1.

In the region of the straight portion 3, the wall thickness is greater than the material thickness 12 in the curved portion, as can be seen in the cross-sectional views in FIGS. 3 to 5:

Whereas the curved portion also has a U-shaped outer contour 7, that outer contour changes at the point of transition into the straight portion, as shown in FIG. 4, to an approximately rectangular cross-section, the side thereof which is opposite from the open side having a U-shaped opening 6 forms a shallow channel 10 extending in the longitudinal direction of the extended body 2.

In the direction towards the securing flange 1, the wall thickness of the straight portion increases, as does also the depth of the channel opposite the open side, the cross-sectional shape of the channel being concavely curved.

This cross-sectional shape is shown in FIG. 3, and it can be seen that in that region of the straight portion 3 the smallest distance 11 between the deepest point of the channel 10 and the deepest point of the U-shaped opening 6 is considerably greater, by approximately a factor of 2, than the wall thickness 12 in the curved portion 4 of the extended body. In addition, the wall thickness inside the cross-section, as shown in FIG. 3, increases from the free ends of the profile towards the region remote therefrom, so that the thickness of the profile in the region of the free ends is less than in the region of smallest distance 11, where it is approximately twice the wall thickness 12.

Also in the straight portion 3 of the tube body the height 21 of the tube body in the vicinity of the smallest distance 11 is greater than the height 23 in the vicinity of the U-shaped opening 6.

Figure 6:
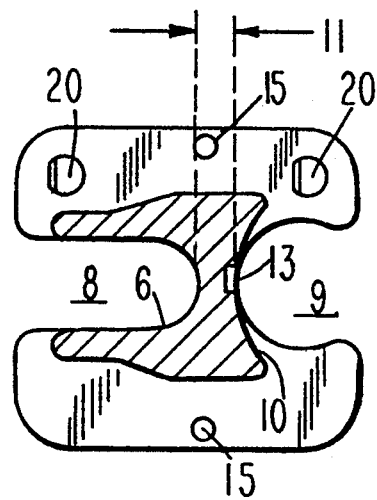
FIG. 6 is a front view of the securing flange.

As shown in FIG. 6, the cross-sectional shape shown in FIG. 3 is retained over the region of the short, straight portion 3 and is present also at the transition to the securing flange 1, where it opens, without a step, into the U-shaped first recess 8, which corresponds to the U-shaped opening 6 of the extended body, and into a second, C-shaped, recess 9 that is located opposite this first recess 8 and is used for snapping a tracheal tube into place. This C-shaped second recess is of a diameter smaller than the width of the channel 10 in the outer side of the straight portion 3, but the deepest point or base of the channel 10 is in alignment with the deepest point or base of the C-shaped second recess 9. Also in alignment therewith is one edge of the extension piece 13, which projects from the securing flange 1 in the direction away from the extended body, so that a tracheal tube that has been pressed into the recess 9 can be secured by winding plaster or the like around the extension piece 13. In order to prevent an adhesive tape piece T from slipping off, the extension piece 13 has at its free end a thickened portion 14 which does not, however, extend into the region of the C-shaped recess 9 to prevent a tracheal tube from lying flat along the outer side of the extension piece 13.

Extending in the same direction are two nipples, arranged one above and one below the recesses 8 and 9, approximately in the center of the securing flange 1, which nipples likewise have a thickened free end but are shorter than the extension piece 13. The ends of the fastening or rubber band 27 provided with suitable slits can be pressed over those nipples 15, the rubber band being fastened around the rear of the head or the neck of a patient to secure the oropharyngeal tube.

The combination of the manufacturing material chosen, for example polyethylene or EVA, together with the dimensioning of the oropharyngeal device, has the result that the straight portion 3 is extremely resistant, rigid and bite-resistant but the long curved portion 4 is not completely rigid but is somewhat elastic, so that the introduction of the device according to the invention is associated with little risk of injury to the patient. The rigidity of the curved portion 4 is nevertheless sufficient to prevent the open profile being compressed by the muscle action of the patient.

While the invention has been illustrated and described as embodied in an oropharyngeal tube, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

I claim:

1. Oropharyngeal device comprising
an extended body including a comparatively shorter approximately straight portion and a comparatively longer curved portion adjoining the straight portion, said extended body having a substantially constant U-shaped transverse cross-section along the entire length of the extended body to provide a U-shaped opening on one side thereof;
a transverse securing flange attached to an end of the straight portion remote from the curved portion, one side of the transverse securing flange being provided with a U-shaped first recess, said first recess conforming to the U-shaped transverse cross-section the extended body and positioned to provide a mouth for the U-shaped opening, and also with a C-shaped second recess in a side of the transverse securing flange remote from the side having the U-shaped first recess, said C-shaped second recess being dimensioned so that an endotracheal tube can be snapped in the second recess and held fixed therein; and
a hard bite block formed integrally with the extended body and located in the vicinity of the straight portion, said bite block being made of a material also used for making the extended body.

2. Oropharyngeal device according to claim 1, wherein the curved portion has a wall thickness such that the extended body is elastic over the entire length thereof but cannot be closed by compression in operation.

3. Oropharyngeal device according to claim 1, wherein the extended body has a longitudinally extending channel on a side opposite to the U-shaped opening, said channel having a base in alignment with a base of the C-shaped second recess for the endotracheal tube.

4. Oropharyngeal device according to claim 3, wherein the channel is concave.

5. Oropharyngeal device according to 3, wherein a smallest distance between the longitudinally extending channel and the U-shaped opening of the extended body is greater than a wall thickness of the extended body.

6. Oropharyngeal device according to claim 5, wherein a height of the cross-section in the straight region of the extended body is greater in the vicinity of the smallest distance than in the vicinity of the U-shaped opening.

7. Oropharyngeal device according to claim 3, further comprising at least one perpendicularly projecting extension piece extending from the transverse securing flange oppositely from the extended body and from a position in the vicinity of the base of the C-shaped second recess.

8. Oropharyngeal device according to claim 7, wherein the extension piece has a length approximately equal to at least a width of an adhesive tape piece and has a thickened portion at a free end thereof.

9. Oropharyngeal device according to claim 1, further comprising two fastening means for insertion into a fastening band, said fastening means being attached to the transverse securing flange and extending from the transverse securing flange oppositely from the extended body.

10. Oropharyngeal device according to claim 9, wherein each of the fastening means has a projecting nipple protruding above and below a center of the transverse securing flange and the transverse securing flange is provided with two eyelets.

11. Oropharyngeal device according to claim 1, wherein a wall thickness of the straight portion is about twice as large as that of the curved portion.

* * * * *